United States Patent [19]

Pagan

[11] Patent Number: 5,895,408
[45] Date of Patent: Apr. 20, 1999

[54] NASAL CLEANING INSERT

[76] Inventor: Gaspar Pagan, Carolina P.R. BQ 27 No. 37 Villa Asturias, San Juan, Puerto Rico 00983

[21] Appl. No.: 08/893,291

[22] Filed: Jul. 15, 1997

[51] Int. Cl.$^6$ .................................................. F24J 2/38
[52] U.S. Cl. ........................ 606/199; 606/161; 606/162; 606/199; 606/196; 604/2; 604/1; 604/3
[58] Field of Search ................................. 606/161, 162, 606/199, 196, 202, 191, 160; 604/2, 1, 3

[56] References Cited

U.S. PATENT DOCUMENTS

| | | | |
|---|---|---|---|
| 1,221,231 | 4/1917 | Sharp | 604/3 |
| 1,381,829 | 6/1921 | Hartman | 606/162 |
| 2,691,985 | 10/1954 | Newsom | 606/196 |
| 4,286,596 | 9/1981 | Rubinstein | |
| 4,863,422 | 9/1989 | Stanley | 604/3 |

*Primary Examiner*—Michael Buiz
*Assistant Examiner*—Lien Ngo
*Attorney, Agent, or Firm*—J. Sanchelima

[57] ABSTRACT

A device to be used for daily cleaning a user's internal walls of his or her nasal cavities. The device is elongated with two ends and an increasing diameter away from the ends. The device is made out of a soft material that conforms to the space defined by the internal wall of a user's nasal cavities. An inner elongated and longitudinally extending core made out of a firmer material is used to enhance the overall resiliency of the device. A plurality of soft filaments extend from the outer surface of the elongated body that with the longitudinally disposed grooves trap the secretions and facilitate their removal. Inserting the device causes it to exert an outwardly radial pressure to aid in the impregnated on the device to provide a user with relief and/or therapeutic treatment.

12 Claims, 3 Drawing Sheets

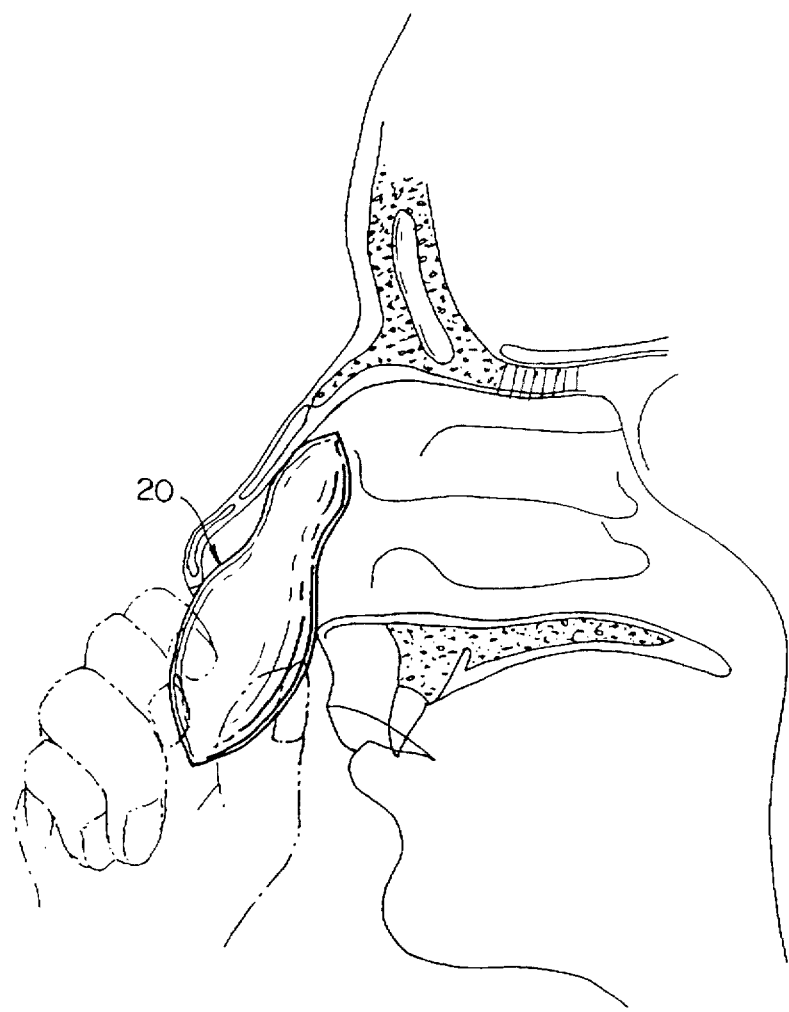
FIG - 1 -
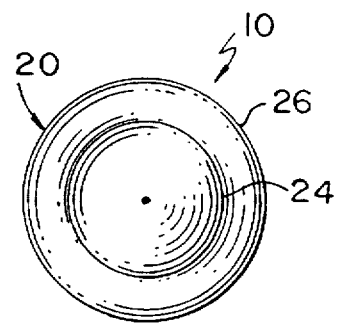
FIG - 3 -

U.S. Patent   Apr. 20, 1999   Sheet 3 of 3   5,895,408
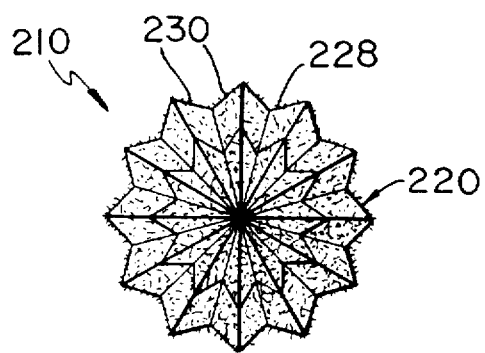
FIG. 5.
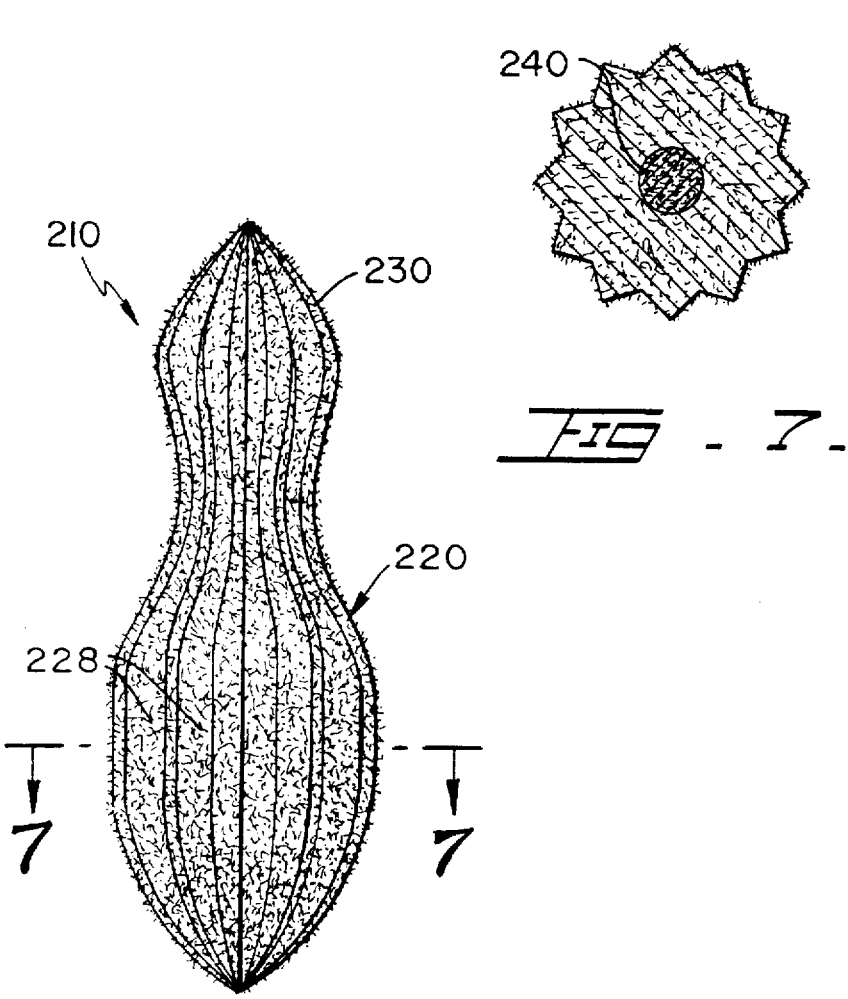
FIG. 7.
FIG. 6.

5,895,408

NASAL CLEANING INSERT

BACKGROUND OF THE INVENTION

1. Field of the Invention

The present invention relates to a cleaning insert, and more particularly, to the type that can be inserted inside the nasal cavities.

2. Description of the Related Art

Most of the cold germs are reproduced in the nasal mucous media enhanced by the humidity of the area. Cleaning periodically the mucous substance inside the nasal cavities after the first sneeze can prevent the cold germs from penetrating the respiratory system.

Applicant believes that the closest reference corresponds to U.S. Pat. No. 4,286,596 issued to Rubinstein in 1981. However, it differs from the present invention because Rubinstein discloses an intravaginal tampon that would not work as the present invention without injuring a user. First, the patented tampon teaches the use of a "highly" absorbable material. The nasal cavity is surrounded by many sensitive nerve terminations and blood vessels and removing all liquids of the mucous would injure a user, as Rubinstein's patent teaches for intravaginal application. While the present invention is intended to clean the mucous, it is to intended to remove all liquids leaving the nasal cavity without a lubricant whatsoever. Also, the rigid cone 15 disclosed in Rubinstein's device would injure a user. The requirements for a vaginal or rectal tampon are different that those needed in the present invention. Also, the present invention, in addition to being used and interact with a different kind of body cavity, is by contrast a "cleaning device" and, Rubinstein's tampon is designed to stop the outflow of substances from the body cavity. The present cleaning device removes mucous substances and germs, and does not plug the cavity. Another difference is that the present invention has no grasping elements mounted to the cleaning body because this device is designed to be used in a short period of time since the respiratory system could not be obstructed for long period of time.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide an ergonomically designed device that permits a user to clean her or his nasal cavities periodically, and even in remote areas where a user does not reach with his or her handkerchief.

It is another object of this invention to provide a nasal cleaning device with impregnated substances for cleaning and refreshing purposes.

It is another object of this invention to provide a device to be used in a short period of time with minimum discomfort to the user.

It is another object of the present invention to provide a device for cleaning nasal cavities that includes small and soft filaments or bristles to dislodge foreign material and germs from the nasal cavities and preventing them from passing to the lungs.

It is another object of the present invention to provide a device for cleaning nasal cavities that includes grooves along the length thereof that permit the user's inhaling and exhaling air to pass through while this device is in use.

It is still another object of the present invention to provide a device that has such a configuration and flexibility that is suitable for users with nostrils of different dimensions.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 show an application of the present invention being manipulated by a user cleaning his/her nasal cavities.

FIG. 3 is a top view of the embodiments shown in FIG. 2.

FIG. 5 is a top view of another alternative embodiment for the present invention, having grooves and filaments mounted thereon.

FIG. 6 is an elevational side view of the embodiment shown in FIG. 5.

FIG. 7 shows a cross-sectional view of the device shown in FIGS. 5 and 6, representing the firmer centrally and longitudinally disposed core.

DETAILED DESCRIPTION OF THE PREFERRED EMBODIMENT

Figure 2:
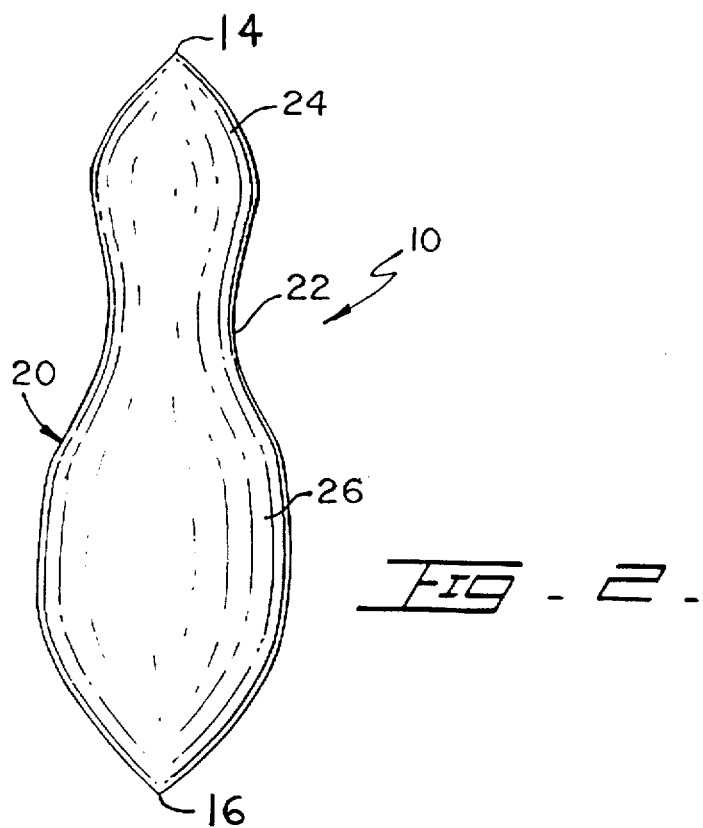
FIG. 2 is elevational side view of one of the preferred embodiments for the present invention.

Infection is caused by a variety of bacteria and germs that live and grow in the nasal cavities. Any obstruction in these cavities, such as polyps, large adenoids, or a deviated septum, may interfere with normal sinus drainage and open the way for infection. That is the reason why the present invention is important to prevent infections that originate in the nasal cavities.

Referring now to the drawings, where the present invention is generally referred to with numeral 10, it can be observed that it basically includes elongated cleaning body 20 with central portion 22 and two side contact portions 24 and 26 adjacent to ends 14 and 16, respectively. The present invention is introduced into the nose removing the mucous poured out from globlet cells and in this manner avoiding the incubation of any possible bacteria or germs.

Elongated cleaning body 20, in the preferred embodiment, has contact portions 24 and 26 which are designed with different peripheral dimensions to permit a child or adult to use device 10. A user inserts cleaning body 20 by aligning end 14 (or 16) with the nostrils' openings. Contact portion 24 (or 26) has a larger diameter as it separates from end 14 (or 16) to ensure that sufficient pressure against the nasal cavities' walls is applied. Narrower end 14 applies less radial pressure inside a user's nasal cavities than end 16. The radial pressure increases as a user introduces device 10 and portion 24 (or 26) penetrates. For adults, end 16 may be used while end 14 is reserved for children or persons with smaller nasal cavities.

Figure 4:
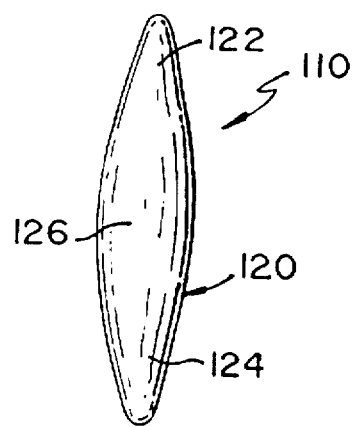
FIG. 4 represents an alternate embodiment for the present invention.

An alternate embodiment 110 is shown in FIG. 4 having substantially an oblique shape with cleaning body 120 with its diameter increasing as its center is approached. The radial pressure on the internal surfaces of the nasal cavities is thus increased with the penetration of device 110. This embodiment is symmetrical. Embodiment 110 includes central contact portion 126 and portions 122 and 124 with smaller diameter.

Another alternate embodiment 210 is shown in FIGS. 5 through 7. Cleaning body 220 includes grooves 228 and soft filaments 230. Filaments 230 are relatively short and flexible. Their function is to comb the nasal hairs and drag any mucous material along. Grooves 228 extend longitudinally along elongated cleaning body 220 and are designed for two purposes: permit a user to breath while he/she is using nasal cleaning insert 210 and to store the nasal secretions as device 10 sweeps the inner surfaces of the nasal cavities and hair. To clean the latter, a user may rotate device 210 for better efficiency. This prevents any pressure build up as the insert is introduced since it may be uncomfortable, specially with congested users. Also, grooves 228 enhance the structural rigidity of insert 210 to facilitate its penetration in the nasal cavity even though a relatively soft material is used. Filaments 230 extend radially outwardly from the outer surface of insert 210. Filaments 230 are intended to increase the effective contact area for dislodging mucous including specially from the user's hair in his/her nasal cavities. Filaments 230 are soft to minimize discomfort the user.

Cleaning bodies 20; 120 and 220 may be selectively impregnated with substances such as camphor, eucalyptus, menthol, or other substance with antihistaminic properties which serve cleaning and refreshing purposes. Other medicament can also be impregnated in bodies 20; 120 and 220 for medical purposes.

Cleaning bodies 20; 120 and 220 are made out of a soft resilient material that is readily deformed as it passes through the nasal cavities, such as spongy material. To enhance the structural integrity of devices 10; 110 and 210, the central portion is provided with elongated longitudinally extending paper fiber core 240 that enhances their resiliency, as shown in FIG. 7. Filaments like those indicated with numeral 230 can also be present in cleaning bodies 20 and 120.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A device for cleaning a user's internal walls and hair of his or her nasal cavities, comprising an elongated body having first and second ends said device having an increasing diameter away from said first and second ends, said elongated body being made of a soft material with a relatively firmer centrally and longitudinally extending core thereby conforming to a user's nasal cavity while exerting sufficient radial and outwardly pressure against the internal walls, and said elongated body further including a plurality of longitudinally extending grooves for storing the nasal secretions swept from said internal walls and hair.

2. The cleaning device set forth in claim 1 further including a plurality of soft filaments mounted on said elongated body.

3. The cleaning device set forth in claim 2 wherein said elongated body includes first and second portions adjacent to said first and second ends, respectively, and said first and second portions having each area separating said first and second portions with a diameter that is relatively smaller than the diameter of said first and second portions.

4. The cleaning device set forth in claim 3 wherein said cleaning device is impregnated with a predetermined cleansing compound.

5. The cleaning device set forth in claim 4 wherein said compound has antihistaminic properties.

6. The cleaning device set forth in claim 5 wherein said compound is camphor.

7. The cleaning device set forth in claim 6 wherein said compound is eucalyptus.

8. The cleaning device set forth in claim 3 wherein said second portion has a diameter that is larger than said first portion's diameter.

9. The cleaning device set forth in claim 8 wherein said cleaning device is impregnated with a predetermined compound.

10. The cleaning device set forth in claim 9 wherein said compound has antihistaminic properties.

11. The cleaning device set forth in claim 10 wherein said compound is camphor.

12. The cleaning device set forth in claim 11 wherein said compound is eucalyptus.

* * * * *